United States Patent [19]

Jones et al.

[11] Patent Number: 5,573,699
[45] Date of Patent: *Nov. 12, 1996

[54] DEODORANT SOAP OR DETERGENT COMPOSITION

[75] Inventors: Keith A. Jones, Lambertville; Janet G. Gardella, Howell, both of N.J.; Todd W. Domke, Newtown, Pa.

[73] Assignee: Church & Dwight Co., Inc., Princeton, N.J.

[*] Notice: The term of this patent shall not extend beyond the expiration date of Pat. No. 5,403,506.

[21] Appl. No.: 412,369

[22] Filed: Mar. 29, 1995

Related U.S. Application Data

[63] Continuation-in-part of Ser. No. 129,427, Sep. 30, 1993, Pat. No. 5,403,506.

[51] Int. Cl.[6] ............................. C11D 9/00; C11D 9/18
[52] U.S. Cl. ............................. 510/131; 510/133
[58] Field of Search ................ 252/108, 174.14, 252/116, 128, 131

[56] References Cited

U.S. PATENT DOCUMENTS

| | | | |
|---|---|---|---|
| 3,284,363 | 11/1966 | Bright | 252/107 |
| 4,322,308 | 3/1982 | Hooper et al. | 252/107 |
| 4,587,029 | 5/1986 | Brooks | 252/91 |
| 4,933,101 | 6/1990 | Cilley et al. | 252/99 |
| 5,000,870 | 3/1991 | Shimizu | 252/183.11 |
| 5,403,506 | 4/1995 | Jones | 252/108 |

*Primary Examiner*—Anthony McFarlane
*Assistant Examiner*—Patricia L. Hailey
*Attorney, Agent, or Firm*—Irving M. Fishman

[57] ABSTRACT

The disclosure describes deodorant soap or detergent compositions comprising a surfactant, e.g., a soap or synthetic detergent, and as a deodorizing component, a minor amount of a sodium zinc carbonate hydrate complex salt. The latter salt may be prepared by reacting zinc oxide and sodium bicarbonate in the presence of water.

10 Claims, 3 Drawing Sheets

DEODORANT SOAP OR DETERGENT COMPOSITION

CROSS REFERENCE TO RELATED APPLICATION

This application is a continuation-in-part of application Ser. No. 08/129,427, filed Sep. 30, 1993 by K. A. Jones, now U.S. Pat. No. 5,403,506.

BACKGROUND OF THE INVENTION

1. Field of the Invention

The invention relates to a novel deodorant toilet soap or detergent composition.

2. Background Information Including Description of Related Art

Perspiration produced directly by the sweat glands of the body are generally odorless or have an innocuous odor. However, unpleasant body odors are often caused by the breakdown of the components of such perspiration by bacteria to produce foul-smelling substances such as butyric acid. Thus, deodorant detergent compositions, e.g., soaps, have been developed containing any of various additives known to act as bactericides or bacteriostats in order to keep the bacteria population on the skin low and hence minimize the breakdown of the perspiration components. It has been found, however, that the most widely used of these additives have certain disadvantages. For example, hexachorophene which was extensively used as a deodorizing additive for several years, has been shown to have a degree of neurotoxicity causing the U.S. Food and Drug Administration to prohibit its use unless prescribed by a physician. Triclocarban (3,4,4'-trichlorocarbanilide), which is presently used in many deodorant soaps, has been found to be a skin irritant in some instances. Thus, any deodorant detergent composition which does not have these disadvantages would be highly desirable.

U.S. Pat. No. 3,284,363, issued Nov. 8, 1966 to Bright, discloses germicidal soaps containing a combination of 3,4,5'-tribromsalicylanilide and 3,4,4'-trichlorocarbanilide (triclocarban) as germicides.

U.S. Pat. No. 4,322,308, issued Mar. 30, 1982 to Hooper et al., discloses a deodorant detergent composition comprising a detergent active compound, a deodorant perfume, and a deodorant other than a deodorant perfume, which may be a zinc "salt" such as zinc oxide.

U.S. Pat. No. 4,587,029, issued May 6, 1986 to Brooks, discloses an intermediate product for use in producing a detergent bar, comprising a sodium salt of a fatty alcohol sulfuric acid or ethoxylated fatty alcohol sulfuric acid and sodium bicarbonate.

U.S. Pat. No. 4,933,101, Issued Jun. 12, 1990 to Cilley et al., disclose liquid automatic dishwashing compositions containing an insoluble inorganic zinc "salt", e.g., zinc oxide, useful for inhibition of glassware corrosion, and a buffering agent which may be sodium bicarbonate.

U.S. Pat. No. 5,000,870, issued Mar. 19, 1991 to Shimizu, discloses a process for converting waste cooking oil to a soap or detergent by cooking the oil with a substance comprising an alkali metal carbonate such as sodium bicarbonate and a component having deodorization capabilities such as zinc oxide.

Application Ser. No. 08/342,304, filed Nov. 18, 1994, now abandoned, discloses a method for preparing a water-insoluble salt comprising a sodium zinc carbonate hydrate formed by reacting zinc oxide with sodium bicarbonate. The entire disclosure relating to the nature of the salt and its method of preparation is incorporated herein by reference.

Application Ser. No. 08/341,750, filed Nov. 18, 1994, now abandoned, discloses dentifrices containing a sodium zinc carbonate hydrate salt formed by reacting zinc oxide with sodium bicarbonate. The entire disclosure relating to the nature of the salt and its method of preparation is incorporated herein by reference.

SUMMARY OF THE INVENTION

In accordance with the invention, a deodorant soap or detergent composition is provided containing a surfactant, e.g., a soap or synthetic detergent, and as a deodorizing component, a minor but effective amount, of a water-insoluble complex salt comprising a sodium zinc carbonate hydrate and optionally, minor amounts of a zinc carbonate and/or unreacted zinc oxide, which may be prepared by reacting sodium bicarbonate with zinc oxide in the presence of water. The composition is particularly useful as a personal toilet soap or detergent composition.

DETAILED DESCRIPTION OF THE INVENTION

Figure 1:
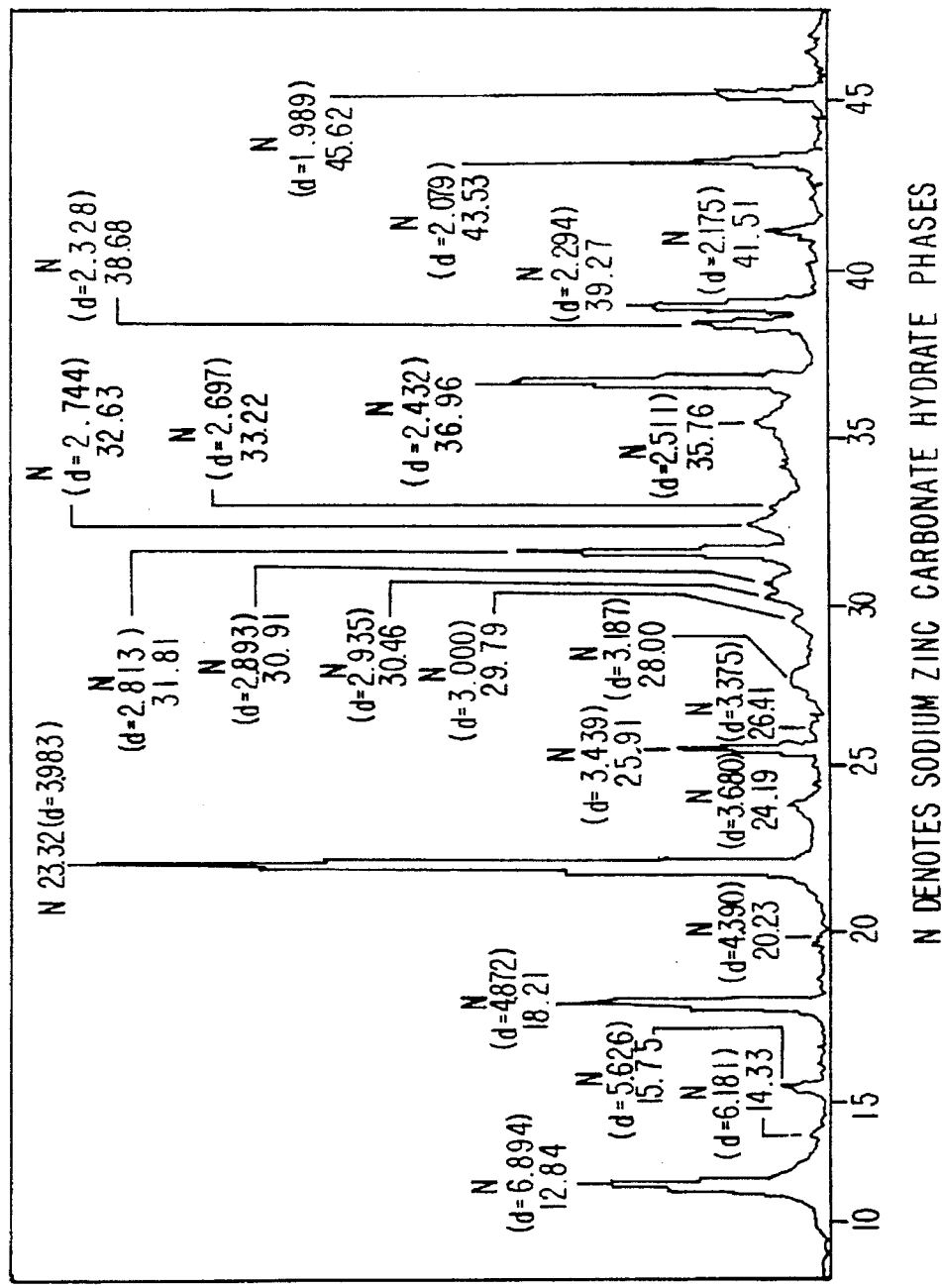
FIGS. 1 to 3 are the X-ray diffraction patterns for the sodium zinc carbonate hydrates prepared using the "SACHTOTEC" agglomerated submicron zinc oxide, the "Z-Cote" agglomerated submicron zinc oxide, and USP grade zinc oxide from Zinc Corporation of America (ZCA), respectively.

The soap and detergent compositions of this invention are solid or liquid and comprise a surface active or surfactant component, e.g., a soap or synthetic detergent, which contains a relatively polar hydrophilic group and a relatively non-polar hydrophobic group. The soaps are salts of relatively long chain fatty acids having the formula R—COO$^-$ X$^+$, where R is often an unbranched saturated or unsaturated aliphatic group but may contain branches or even ring groups. Thus, the carboxylate (—COO$^-$) groups constitute the hydrophilic groups of the soap molecule while the long carbon chain R groups constitute the hydrophobic groups. In order for the soap to have adequate solubility in water, the cation of the soap, X$^+$, is usually an alkali metal, e.g., sodium or potassium, or, more rarely, an ammonium or substituted ammonium group.

Typical soaps contemplated under this invention are the water-soluble alkali metal, e.g., potassium and sodium, soaps of the saturated and unsaturated higher fatty acids having from about eight to about twenty-six carbon atoms, such as capric, caprylic, lauric, myristic, palmitic, stearic, oleic, linoleic, linolenic, arachidic, behenic, margaric, tridechoic, and cerotic acids and the mixtures of such acids naturally occurring in fats, oils, waxes and rosins, such as the soaps of coconut oil fatty acids, tallow fatty acids, pig fat, fish oil fatty acids, beeswax, palm oil fatty acids, sesame oil fatty acids, peanut oil fatty acids, olive oil fatty acids, palm kernel oil fatty acids, cottonseed oil fatty acids, soybean oil fatty acids, corn oil fatty acids, babassu oil fatty acids, rosin acids, abietic acid and greases.

Solid soaps generally comprise a predominantly sodium salt of longer chain and/or more saturated carboxylic acids present in a composition containing a relatively small amount of water. In contrast, the surfactant of a liquid soap often contains a substantial proportion of potassium and/or ammonium cations in place of or in addition to sodium ions. Moreover such liquid soap surfactant is usually a salt of a shorter chain and/or more unsaturated carboxylic acid, and is mixed with a larger percentage of water.

The synthetic detergents contemplated as surfactants under this invention are compounds other than soap whose detersive properties, like soap, are due to the presence of a hydrophilic and a hydrophobic group in the molecule. However, unlike soaps, synthetic detergents are not salts of carboxylic acids derived from fats and oils. Rather, the hydrophilic portion of the surfactant of a synthetic detergent is generally derived from a compound containing a relatively long carbon chain, e.g., a hydrocarbon obtained from petroleum refining and/or olefin polymerization or a long chain fatty acid, while the hydrophilic portion is the result of chemical modification of such compound to introduce the desired polar group, e.g., a hydroxyl, sulfate or sulfonate group.

The synthetic detergent compositions of this invention generally contain at least one anionic or nonionic surfactant or a mixture of the two types of surfactant.

The contemplated water soluble anionic detergent surfactants are the alkali metal (such as sodium and potassium) salts of the higher linear alkyl benzene sulfonates and the alkali metal salts of sulfated ethoxylated and unethoxylated fatty alcohols, and ethoxylated alkyl phenols. The particular salt will be suitably selected depending upon the particular formulation and the proportions therein.

The sodium alkybenzenesulfonate surfactant (LAS) most preferably used in the composition of the present invention has a straight chain alkyl radical of average length of about 11 to 13 carbon atoms.

Specific sulfated surfactants which can be used in the compositions of the present invention include sulfated ethoxylated and unethoxylated fatty alcohols, preferably linear primary or secondary monohydric alcohols with $C_{10}$–$C_{18}$, preferably $C_{12}$–$C_{16}$, alkyl groups and, if ethoxylated, on average about 1–15, preferably 3–12 moles of ethylene oxide (EO) per mole of alcohol, and sulfated ethoxylated alkylphenols with $C_8$–$C_{16}$ alkyl groups, preferably $C_8$–$C_9$ alkyl groups, and on average from 4–12 moles of EO per mole of alkyl phenol.

The preferred class of sulfated ethoxylated surfactants are the sulfated ethoxylated linear alcohols, such as the $C_{12}$–$C_{16}$ alcohols ethoxylated with an average of from about 1 to about 12 moles of ethylene oxide. A most preferred sulfated ethoxylated detergent is made by sulfating a $C_{12}$–$C_{15}$ alcohol ethoxylated with 3 moles of ethylene oxide.

Specific nonionic surfactants which can be used in the compositions of the present invention include ethoxylated fatty alcohols, preferably linear primary or secondary monohydric alcohols with $C_{10}$–$C_{18}$, preferably $C_{12}$–$C_{16}$, alkyl groups and on average about 1–15, preferably 3–12 moles of ethylene oxide (EO) per mole of alcohol, and ethoxylated alkylphenols with $C_8$–$C_{16}$ alkyl groups, preferably $C_8$–$C_9$ alkyl groups, and on average about 4–12 moles of EO per mole of alkyl phenol.

The preferred class of nonionic surfactants compounds are the ethoxylated linear alcohols, such as the $C_{12}$–$C_{16}$ alcohols ethoxylated with an average of from about 1 to about 12 moles of ethylene oxide. A most preferred nonionic detergent is a $C_{12}$–$C_{15}$ alcohol ethoxylated with 3 moles of ethylene oxide.

Mixtures of the foregoing synthetic detergent type of surfactants, e.g., of anionic and nonionic, or of different specific anionic or nonionic surfactants, may be used to modify the detergency, lather characteristics, and other properties of the composition. For example, a mixture of different fatty alcohols of 12 to 15 carbon atoms may be ethoxylated, directly sulfated, or sulfated after ethoxylation, a fatty alcohol may be partially ethoxylated and sulfated, or an ethoxylated fatty acid may be partially sulfated to yield a mixture of anionic and nonionic surfactants or different specific anionic or nonionic surfactants.

The water-insoluble salt or salt mixture containing the sodium zinc carbonate hydrate complex salt and optionally a zinc carbonate and/or zinc oxide is prepared by a process which comprises the steps of:

(a) reacting zinc oxide with sodium bicarbonate, typically in an aqueous solution or suspension of sodium bicarbonate, preferably a saturated solution; and (b) recovering the water-insoluble salt or salt mixture.

The reaction may be carried out, for example, at room temperature by suspending zinc oxide in a preformed aqueous solution or suspension containing about 1–50% sodium bicarbonate or by simultaneously adding the zinc oxide and sodium bicarbonate to water and mixing until the reaction to form the complex salt is substantially complete. Preferably, the solution phase of the mixture is at least saturated with sodium bicarbonate. Mixing is usually carried out for a period of, for example, about 10 to 120 minutes.

The salt or salt mixture can be recovered by filtration or centrifugation. Preferably, the resulting salt or salt mixture is washed with water to remove excess sodium bicarbonate.

Figure 2:
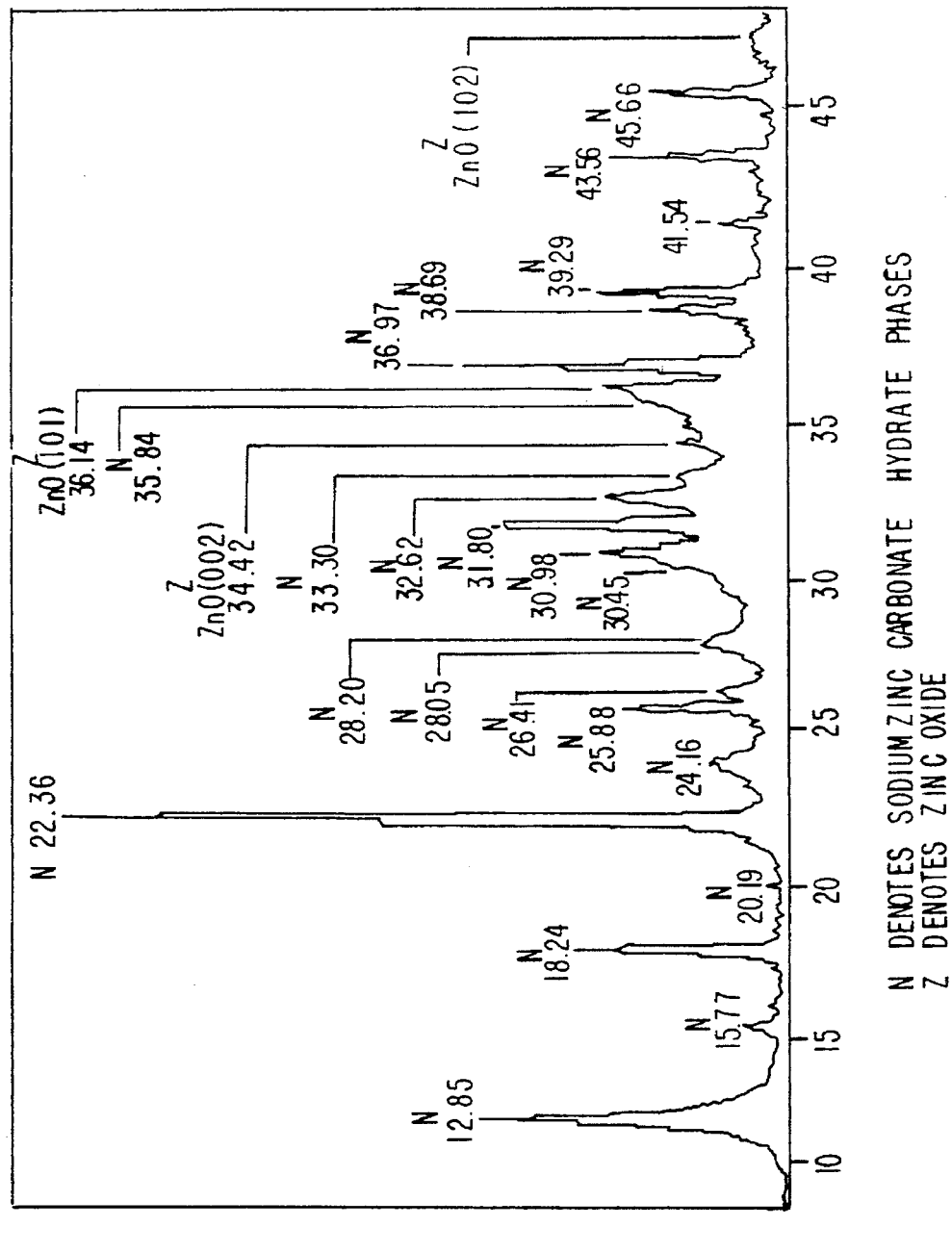
Figure 3:
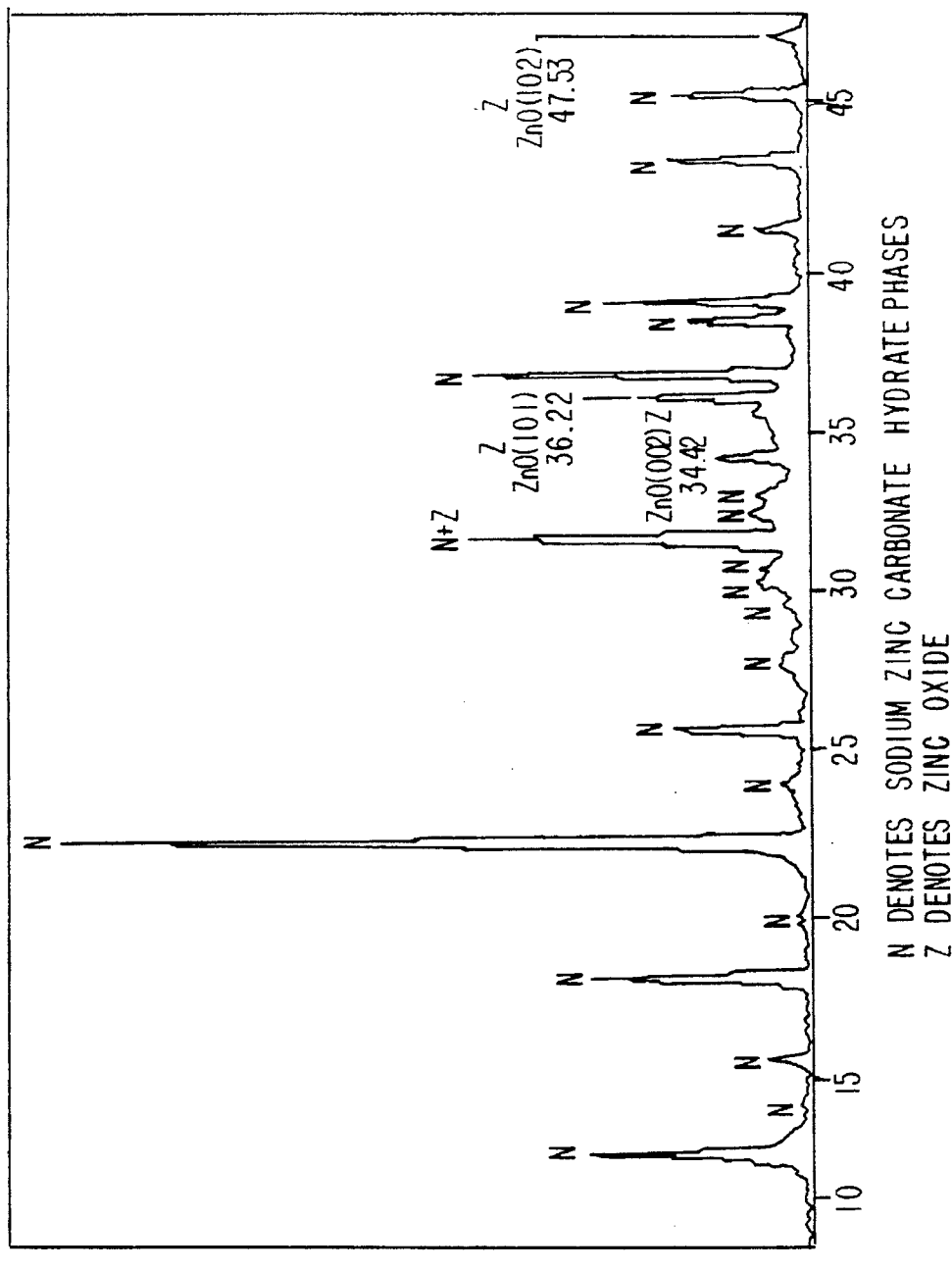

The sodium zinc carbonate hydrate has a unique X-ray diffraction pattern as shown in FIGS. 1–3 and a lattice constant of 13.74 Angstroms. Elemental analysis confirms the presence of sodium, zinc, and carbonate groups.

A significant amount of water and, optionally, other liquids at room temperature such as glycerin must be present before the sodium zinc carbonate hydrate complex salt can be efficiently formed by means of the foregoing process. Thus, in the case of solid soap or detergent compositions which often contain very little water or other compounds liquid at room temperature, the complex salt may be advantageously preformed before compounding it with the solid soap or detergent base composition. However, in the case of solid soap or detergent compositions which do contain sufficient water, or liquid soap or detergent compositions which generally contain, for example, at least about 20 wt. % of water based on the weight of the composition, the complex salt is believed to form in situ when the zinc oxide and sodium bicarbonate are added separately to the water-containing solid or liquid liquid soap or detergent base composition, so that such separate addition of the components may be carried out under these circumstances.

All zinc oxides are suitable for the preparation of the sodium zinc carbonate hydrates including USP grade zinc oxide from Zinc Corporation of America (ZCA). Submicron zinc oxide is preferred, e.g., having a primary particle size range of about 0.005 to 0.5 micron. The most preferred zinc oxide is an agglomerated submicron zinc oxide, suitably having an agglomerate size of about 1 to 10 microns.

Specific, but non-limiting examples of zinc oxides having submicron average particle sizes are available from Sachtleben Chemie under the trademark "SACHTOTEC" from Presperse Inc. under the trademark "Finex 25", and from SunSmart under the trademark "Z-Cote". The SACHTOTEC particles have an average particle size of about 0.20 micron, but the particle size can be as small as 0.005–0.015 micron; the agglomerated particle size is about 4 to 6.5 microns. The Finex 25 particles have a particle size of about 0.1–0.5 micron; the agglomerated particle size is about 4–5 microns. The Z-Cote particles have an average particle size of about 0.1–0.5 micron; the agglomerated particle size is about 1–5 microns.

The sodium zinc carbonate hydrate complex salt contemplated under this invention may contain, for example, about 20 to 40 wt. % of carbonate ($CO_3$), about 2 to 6 wt. % of sodium, about 40 to 65 wt. % of zinc and about 10 to 20 wt. % of water of hydration. The reaction to form the complex salt may be carried out utilizing, for example, about 2 to 50 parts of sodium bicarbonate and at least about 15 parts of water, per part of zinc oxide, all parts being by weight. The finished soap or detergent composition whether solid or liquid, may contain for example about 1 to 25 wt. %, preferably about 5 to 15 wt. % of the sodium zinc carbonate hydrate complex salt, based on the weight of the total surfactant.

The soap or detergent composition of this invention may also contain varying quantities of compatible adjuvants which do not materially interfere with the bactericidal effect of the sodium zinc carbonate hydrate complex salt. Typical of such compatible adjuvants are fillers and pigments such as titanium dioxide, diatomaceous earth, any of various colored pigments, dyes, fragrances, optical brighteners and bactericidal and bateristatic compounds other than zinc oxide such as cetylpyridinium chloride.

The composition may be in solid form such as bars, flakes, chips, or powders or in liquid form. In addition to the possible differences discussed previously in the chemical nature of the active fatty acid salt in solid and liquid soap compositions, solid detergent compositions often contain a significant amount of pigment and filler and little or no water while liquid compositions generally contain no pigment or filler but may contain a significant amount of water, e.g., at least about 20 wt. % based on the weight of the composition, optionally together with other compatible compounds liquid at room temperature, such as glycerin, in which the active soap or synthetic detergent component is soluble.

The sodium zinc carbonate hydrate complex salt may be added to the soap or detergent composition at any point in the conventional manufacture of these products. For example in the production of solid soap bars under the invention, soap chips may be weighed into a mixer, the complex salt of the invention and the contemplated compatible adjuvants, if any, added thereto, and the total mixed for a long enough period to achieve uniformity of the mix. After mixing, the composition can be formed into framed or milled soap bars in accordance with the general procedure of the soap making art.

The following examples further illustrate the invention.

EXAMPLES 1–3

Water insoluble sodium zinc carbonate hydrates complex salts were prepared by reacting sodium bicarbonate ($NaHCO_3$) with each of three samples of zinc oxide (ZnO), two submicron zinc oxides, viz. SACHTOTEC (Example 1) and Z-Cote (Example 2), and an ordinary U.S.P. grade zinc oxide (Example 3). The procedure used was as follows:

Approximately, 3 grams of each zinc oxide was suspended in 100 g. of a filtered, saturated sodium bicarbonate solution (about 10%) and allowed to mix for 1 hour at room temperature. The insoluble material was recovered by filtering through a 0.22 μm filter membrane. It was then resuspended in 100 ml. of distilled water and allowed to mix for 30 minutes to dissolve any soluble sodium bicarbonate and sodium carbonate salts. The insoluble material was recollected by filtration through a 0.22 μm filter membrane, resuspended in 100 ml. of distilled water for a final rinse, collected on a 0.22 μm filter, and dried overnight at room temperature in a desiccator, over phosphorus pentoxide while under vacuum.

The resulting dry powders were analyzed for their total carbonate content ($CO_3$), as well as for the presence of sodium (Na) and zinc (Zn).

The results are shown in Table I.

TABLE I

| Example | Zinc Oxide | $CO_3$ (%) | Na (%) | Zn (%) |
| --- | --- | --- | --- | --- |
| 1 | SACHTOTEC | 32.94 | 4.6 | 48.5 |
| 2 | Z-Cote | 27.65 | 3.4 | 57.4 |
| 3 | ZCA USP | 32.50 | 4.8 | 48.6 |

The remainder to 100% of each complex salt was water of hydration.

All three zinc oxides reacted with sodium bicarbonate were examined by the Debye-Scherrer powder (film) technique as well as X-ray diffractometry in order to counter any preferred orientation effects. The radiation used was Cu K alpha. The new insoluble salt referred to as cubic sodium zinc carbonate hydrate has a lattice constant of 13.74 Angstroms.

Based on the results of the X-ray diffraction analyses, it was estimated that the samples contained the amount of sodium zinc carbonate hydrate, zinc carbonate, and zinc oxide shown in Table II.

TABLE II

| Example | Sodium Zinc Carbonate Hydrate | Zinc Carbonate | Zinc Oxide |
| --- | --- | --- | --- |
| 1 | >90% | <5% | <5% |
| 2 | >90% | <2% | ≈2–8% |
| 3 | ≈90% | — | ≈10% |

To each of three samples of chips of a commercially available soap base composed of a mixture of sodium salts of about 80 wt. % of tallow fatty acids and about 20 wt. % of coconut oil and/or palm kernel oil fatty acids being masticated in a mixing machine at a temperature of about 25° C. are added 0.75 wt. % of titanium dioxide, 0.01 wt. % of tetrasodium ethylenediamine tetraacetic acid (EDTA), 2.50 wt. % of glycerin, 0.5 wt. % of fragrance, 1–2 wt. % of deionized water and 10 wt. % of one of the previously described sodium zinc carbonate hydrate complex salts produced from SACHTOTEC (Example 1), Z-Cote (Example 2) or ZCA USP grade zinc oxide (Example 3). The soap base constitutes about 84–85 wt. % of the total composition. Mastication is continued until a uniform appearing plastic mass is obtained.

The soap compositions of the foregoing examples are found to exert a substantially larger deodorant effect when used in ordinary washing operation than the same compositions containing no sodium zinc carbonate hydrate complex salt.

EXAMPLE 4

A sodium zinc carbonate hydrate complex salt was prepared by adding 1010 grams of SACHTOTEC zinc oxide and 2000 grams of sodium bicarbonate to 10 liters of water and mixing for one hour at room temperature. The insoluble salt was filtered through a No. 1 Whatman filter. The salt was washed by mixing with 10 liters of water for one hour and again filtered through a No. 1 Whatman filter, and the washing and filtering was repeated three more times. The complex salt filter cake was then vacuum drained and air dried overnight. The complex salt was then used to prepare a solid soap composition containing 10 wt. % of such salt as described in Examples 1–3.

The soap composition containing the sodium zinc carbonate hydrate complex salt of this example is found to have a significantly greater deodorant effect than the same soap composition containing no complex salt.

We claim:

1. A toilet deodorant soap or detergent composition comprising a surfactant and as a deodorizing component, about 1 to 25 wt. % based on the total surfactant of sodium zinc carbonate hydrate complex salt.

2. The composition of claim 1 wherein said surfactant is a soap.

3. The composition of claim 2 in the form of a solid bar.

4. The composition of claim 1 wherein said surfactant is a synthetic detergent.

5. The composition of claim 1 wherein said amount of complex salt is about 5 to 15 wt. %.

6. A method comprising washing the human body with the composition of claim 1.

7. A method for making a solid toilet deodorant soap or detergent composition comprising reacting zinc oxide and sodium bicarbonate in the presence of water to form a sodium zinc carbonate hydrate complex salt and mixing said complex salt with a solid surfactant, to form a composition containing about 1 to 25 wt. % of said complex salt based on the total surfactant.

8. The method of claim 7 wherein said zinc oxide is composed of agglomerated submicron particles having a primary particle size of about 0.005 to 0.5 micron and an agglomerated size of about 1 to 10 microns.

9. A method of making a liquid toilet deodorant soap or detergent composition comprising adding zinc oxide and sodium bicarbonate separately to a liquid composition comprising a surfactant and water causing the zinc oxide to react with the sodium bicarbonate to form a sodium zinc carbonate hydrate complex salt which is present in said composition in an amount of about 1 to 25 wt. % based on the total surfactant.

10. The method of claim 9 wherein said zinc oxide is composed of agglomerated submicron particles having a primary particle size of about 0.005 to 0.5 micron and an agglomerated size of about 1 to 10 microns.

* * * * *